United States Patent [19]
Harman et al.

[11] Patent Number: 5,939,282
[45] Date of Patent: Aug. 17, 1999

[54] METHODS OF ASSESSING VIABILITY OF MICROBIAL CULTURES

[76] Inventors: Elizabeth K. Harman, 1099 NE. 134th Ave., Alleman, Iowa 50007; William Michael Rutherford, 4608 Merced, Des Moines, Iowa 50310

[21] Appl. No.: 08/899,404

[22] Filed: Jul. 23, 1997

Related U.S. Application Data

[63] Continuation of application No. 08/555,566, Nov. 8, 1995, abandoned.

[51] Int. Cl.[6] .............................. C12Q 1/02; C12Q 1/00; C12Q 1/68
[52] U.S. Cl. .................................. 435/29; 435/4; 435/6; 435/34; 435/39; 435/40.5; 435/40.51; 435/968; 436/800
[58] Field of Search .............................. 435/4, 6, 29, 34, 435/39, 40.5, 40.51, 968; 436/800

[56] References Cited

U.S. PATENT DOCUMENTS

| | | | |
|---|---|---|---|
| 4,639,421 | 1/1987 | Sage, Jr. ..................................... | 435/34 |
| 5,314,805 | 5/1994 | Haugland et al. ........................ | 435/29 |

OTHER PUBLICATIONS

Kapuscinski, Jan; "DAPI: a DNA–Specific Flourescent Probe", *Biotechnic & Histochemistry*, 70(5):220–233, 1995.
Arndt–Jovin et al., "Fluorescence Labeling and Microscopy of DNA", *Methods in Cell Biology*, 30(16):417–448, 1989.
Becker et al., "In Situ Screening Assay for Cell Viability Using a Dimeric Cyanine Nucleic Acid Stain", *Analytical Biochemistry*, 221:78–84, 1994.
Haugland, Richard P.; "Nucleic Acid Detection", *Handbook of Fluorescent Probes and Research Chemicals*, 8:143–151, 1996.
"SYTO®Live Cell Nucleic Acid Strains", *Molecular Probes*, 1–9, May 15, 1997.
Kaprelyants and Kell. J. Appl. Bacteriol. vol. 72, pp. 410–422, 1992.
Caron and Bradley. J. Microscopy. vol. 179, pp. 55–66, 1995.

*Primary Examiner*—Leon B. Lankford, Jr.
*Assistant Examiner*—Christopher R. Tate

[57] ABSTRACT

The present invention provides methods for rapidly determining the proportion of live, dead and stressed cells in a given microbial culture. The measurement of stressed cells is used as a quantitative indicator of the relative health of the population and the population's ability to withstand long term stress. The present methods comprise the steps of (i) staining the culture with a combination of membrane-permeable and membrane-impermeable stains; and (ii) quantifying the population of stressed cells, using the measurement thus obtained as an indicator of the relative health of the population.

8 Claims, No Drawings

METHODS OF ASSESSING VIABILITY OF MICROBIAL CULTURES

This is a continuation of application Ser. No. 08/555,566 filed Nov. 8, 1995, now abandoned.

FIELD OF THE INVENTION

The present invention relates to methods of predicting the viability and survivability of microbial cultures. Specifically, the present invention relates to methods of predicting the viability of bacterial cells in a population which is subject to typical stresses.

BACKGROUND OF THE INVENTION

Bacterial cultures are widely produced for inclusion in products such as forage inoculants, probiotics and fermented foods. Cultures are typically prepared by fermentation; they are grown in large volumes of enrichment broth, either by shaken-flask, solid-state or continuous fermentation. Once the desired cell population is reached, the cells are harvested from the production fermentor and preserved by cryopreservation and/or lyophilization. See e.g. Manual of Industrial Microbiology and Biotechnology, ASM, Washington, D.C., Demain, A. L., Solomon, N. A. (eds.) (1986). After preservation, cultures may be blended into commercial product and stored.

At each step, from fermentation to commercial product preparation, the cells are subject to constantly changing environments which lead to various types of stress and injury. Typical stresses include pH fluctuations, depletion of essential nutrients and accumulation of metabolic by-products. Concentration and freezing of cells after growth can constitute additional stress.

Freezing often produces cold shock and leads to the formation of intracellular ice. Freeze-drying is typically conducted by sublimation of water. Freeze-dried cultures are stored under refrigeration or frozen in dry, moisture-proof packaging until inclusion in commercial products. When cultures are used in commercial formulations, cells are further insulted due to mechanical injury and long term storage.

The stress on bacterial cultures, from fermentation through commercial product inclusion, lead to cell death and injury. Loss of viable cells due to the above stress results in loss of active product to the end user. Because of decreased viability, the product may not have desired efficacy or meet guaranteed specifications; therefore additional culture is typically included in the commercial product to assure adequate performance. If cultures used to prepare products contain stressed and injured cells, the product may not have stability to withstand the additional stress of long-term storage. Thus, product efficacy may decrease over time. Drop in culture viability results in additional expense to the manufacturer due to product recall or fortification to meet label specifications.

To prevent manufacture of bacterial products with stressed culture, it is necessary to screen cultures for viability and vitality prior to inclusion into a commercial finished product. The usual method for detecting microorganisms is by the conventional plate count method as described by the FDA Bacteriological Analytical Method, Washington, D.C.: *AOAC*, (1984). According to this method, viable microbial cells are placed onto a solid medium, containing all the nutrients essential for growth, and the inoculated medium is incubated under conditions favorable for growth. The cells reproduce on the medium to form visible colonies that comprise cloned generations of the original cell. See Microbial Ecology: Principles, Methods and Applications, Levin, M. A., Seidler, R. J., Rogul, M. (eds), McGraw Hill, Inc., New York, (1992). This method, limited to assessing only those cells which are live, uninjured or capable of recovery on the standard microbial medium, typically requires several days of incubation.

Current practices to determine culture suitability for product inclusion are performed by long-term shelf-life stability studies. This method requires storage of culture under different environmental conditions for up to twelve months. Culture viability counts are verified during the time period in storage by the conventional plate count method described above. This standard procedure requires a long time interval for stability testing during which it is not possible to predict the population of cells most likely to die. Unless the injured cells are recoverable on standard agar, they are not included in the viable population.

Based on the foregoing, there exists a need to provide assay methods to predict the viability of bacterial cells that allow for rapid determination of live, dead and/or stressed cells in a culture. There exists a further need to rapidly evaluate the relative health of a population of cells.

It is therefore an object of the present invention to provide methods of rapidly determining the proportion of live, dead or stressed cells in a culture.

It is a further object of the present invention to provide a rapid quantitative indicator of the relative health of a given population of cells.

It is a further object of the present invention to provide methods of predicting the long-term stability of a given culture.

It is a further object of the present invention to provide means of meeting specifications of a given culture at minimal expense.

These and other objects of the present invention will become readily apparent from the ensuing description.

SUMMARY OF THE INVENTION

The present invention provides a method for rapidly determining the proportion of live, dead and stressed cells in a culture by using a combination of fluorescent stains and fluorescence measurement. The measurement of stressed cells in the population is a quantitative indicator of the relative health of the population. The proportion of stressed cells is also related to the rate of decline in viable counts because these cells are sometimes scored as live or viable plate counts but cannot withstand the added stress of product inclusion or storage. The use of the present method detects this population and gives a relative measure of the long-term stability of the culture.

DETAILED DESCRIPTION OF THE INVENTION

As used herein "live cell" means a cell which has the potential to grow and divide over a wide range of nutrient compositions and environmental conditions.

As used herein "stressed cell" means a cell which may have the ability to grow and divide under a narrow range of nutrient compositions and environmental conditions.

As used herein "dead cell" means a cell which is not capable of growing and dividing.

As used herein "stress" means any situation which compromises the vitality of a cell. Stresses include, but are not limited to pH changes, nutrient deprivation, chemical injury, freeze-drying, mechanical injury, long-term storage, temperature fluctuation and relative humidity changes.

As used herein "membrane permeable" means capable of non-specific transfer across a selective membrane.

As used herein "membrane impermeable" means incapable of moving across a selective membrane.

According to the present invention, cultures are evaluated in their native state to determine the level of different cell populations, live, dead or stressed, to estimate their ability to withstand additional stress. It may also be desirable to subject the cells to an additional controlled stress to evaluate their tolerance to adverse conditions during product formation and long term storage.

The use of a combination of fluorescent probes coupled with fluorescence measurement allows viability assessment of the culture during fermentation, preservation and storage prior to inclusion in commercial products. This allows the selection of the cell cultures with the smallest number of stressed cells to provide optimal long-term stability and efficacy.

The stains useful in the present invention involve a membrane-permeable stain for live staining of a first color, and a membrane-impermeable stain for dead staining of a second color. An intermediate array of colors result if the cells are stressed. The array of colors is distinguishable from both the first color and the second color. In a preferred embodiment, commercial stains used to label bacterial cultures consist of a green fluorescent membrane-permeable nucleic acid stain for live staining, and a red fluorescent, membrane-impermeable stain for dead staining.

Useful stains include fluorescein diacetate, carboxy fluorescein diacetate ("CFDA"), fluorescein isothiocyanate, chemchrome Y, chemchrome B, LIVE/DEAD® Baclight™ Viability Kit (SYTO 9 an asymmetrical cyanine dye having a cyclic substituent as disclosed in U.S. Pat. No. 5,436,134 and propidium iodide) (Molecular Probes®, Eugene, Oreg.), rose bengal, calcein acetoxy methyl ester, Hoechst 33342, rhodamine 123, 3,3' dihexyloxacarbocyanine iodide, Calcofluor white, propidium iodide, 4',6-diamidino-2-phenylindole ("DAPI"), ethidium bromide 3,6-bis[dimethylamino]acridinium chloride (acridine orange) and cyanine dyes. Preferred stains include rhodamine 123, DAPI, LIVE/DEAD® Baclight™ Viability Kit (Molecular Probes®, Eugene, Oreg.), acridine orange, ethidium bromide, carboxy fluorescein diacetate fluorescein diacetate, propidium iodide and cyanine dyes. More preferred stains include carboxy fluorescein diacetate, LIVE/DEAD® Baclight™ Viability Kit (Molecular Probes®, Eugene, Oreg.), and propidium iodide ("PI"). The most preferred stain is LIVE/DEAD® Baclight™ Viability Kit, Molecular Probes®, Eugene, Oreg.

The membrane-permeable stain is able to stain all cells, while the membrane-impermeable stain can only enter cells which have compromised membranes. In a preferred embodiment, live cells are observed as green and dead ones as red. Injured cells allow the uptake of both stains in varying proportions, depending upon the degree of injury, thus emitting light varying from yellow to orange. The exact color depends on the relative amounts of red and green stains permeating the cell membrane. This relative ratio corresponds to the physiological condition of the cell. A large number of stains and dyes are useful for the application of detecting stressed cells either in fresh or freeze-dried culture. The only requisite for the use of a particular set of dyes is that the dyes be differentially permeable to cells depending upon the physiological state of the cell. The exact composition of the staining mixture and ratio of dyes used is highly dependent upon the compound. One skilled in the art can easily determine the proper dye combinations and proportions.

As used herein, "fluorescence" means the light emitted by a compound when excited by shorter wavelength light. As used herein "fluorescence measurement" includes but is not limited to flow cytometry, fluorescence microscopy, fluorescence spectroscopy, fluorescence diode array detection and multiwell fluorescence plate reading.

Flow cytometry is a particularly preferred fluorescence measurement. It combines the advantage of microscopy and biochemical analysis for the measurement of physical or chemical characteristics of individual cells as they move in a fluid stream past optical or electronic sensors. See Muirhead, K. A., Horan, P. K. and Poste, G. "Flow Cytometry: Present and Future"; *Biotechnol.*, Vol. 3, 337–356 (1985). Cells are stained with fluorescent probes specific for cell functions or properties. When these cells pass through a laser beam, fluorescence is detected at an angle perpendicular to the laser beam. A 45 degree dichroic mirror reflects the scattered laser light to a detector, while longer wavelengths of fluorescence pass through. Fluorescence separation of up to four colors (such as green, orange, red and long red) is achieved with additional filters specific for each color detector.

The following guidelines and standards are preferred for selecting suitable culture for inclusion into commercial product. One skilled in the art can easily vary the following procedure according to given specifications. Upon receipt, batches of lyophilized culture are randomly sampled and analyzed by fluorescence measurement for populations of live, dead and stressed cells using selected fluorescent probes. Each lot having an initial intermediate population of less than 10% and a live population of greater than 70% is subject to a standard stress model of increased heat and humidity and re-analyzed. Unstressed and stressed samples are compared to determine which culture lots show the highest stress tolerance. Stress tolerance is defined as the reduction in the live population to no less than 50% and an increase in the intermediate population to no more than 35% under standard stress conditions described in the examples below. In all cases, the percentage of the particles falling in a particular category is a percentage of the total fluorescent particles and does not include the debris with little or no fluoresence.

Although the use of the flow cytometer provides the ability to measure thousands of cells in a few minutes, it is also possible to obtain population differences with the use of a microscope equipped with reflected light fluorescence equipment and filters specific to selected fluorescent probes.

Suitable stains for use in such a technique include CFDA, a membrane-permeable stain for live cells and PI, a membrane-impermeable nucleic acid stain for dead cells. A fluorescent microscope equipped with any standard fluorescein long-pass filter is able to view the fluorescence from live (green), dead (red) and stressed (orange) cells.

The PI concentration of 0.5–10 $\mu$g/ml and CFDA concentration of 10–200 $\mu$g/ml is sufficient to stain cells depending upon the cell type. Once cells are stained they are kept in the dark at room temperature for 15 minutes. The stained cell suspension is inoculated at an appropriate dilution into a Petroff-Hausser Counting Chamber. Cells are counted under the fluorescent microscope differentiating between green, orange and red cells. Using these stains and the microscope, cultures which are unstressed and stressed are evaluated as to their suitability for product inclusion.

The present invention can be better understood by referring to the following detailed examples which illustrate various applications, but are in no way intended to limit the scope thereof.

EXAMPLE 1

Two lots of freeze-dried, stabilized culture, stored in moisture vapor barrier packaging at 4° C., are evaluated for their relative proportions of live, dead and stressed cell populations. Cultures are resuspended in normal saline and serially diluted to a concentration of one million cells/ml. A sample of the diluted cells is stained with a commercially available bacteria viability kit (LIVE/DEAD Baclight Viability Kit, (Molecular Probes®, Eugene, Oreg.) according to the manufacturer's protocol. The stained sample is analyzed by flow cytometry to measure the cells fluorescing red, green and the various hues of yellow and orange. In all samples, 50,000 total particles are analyzed by forward angle light scatter.

Cell cultures are stained with the green (live) stain only and then the red only (dead) stain. From this individual staining procedure one can determine where on the graphic representation (e.g. histogram) cells with only green or red are located. The user can mark or "gate" a population of cells in a specific area and overlay these gates on other histogram displays for comparison. This gating procedure is known as an analysis protocol.

An analysis protocol is created indicating the different populations. The live population has intense green fluorescence while the stressed population, has a combination of both red and green stains. The dead population, contains red cells with no green fluorescence. A separate region represents debris with little or no fluorescence in either the red or green areas.

A comparison is made between two bacteria cultures of *Enterococcus faecium* prepared from different fermentation batches and of different ages, each having a different long-term stability. The first culture shows a population of cells representing 78.8% live cells and 12.5% stressed cells staining both red and green. The second culture is more stressed, with only 37.8% of live cells and 57.8% stressed cells.

The injured cells are readily discernible from live and dead cells by fluorescence staining and flow cytometery.

EXAMPLE 2

Two lyophilized cultures of *Enterococcus faecium* (cultures 1 and 2) are stored for ten days at 37° C. and 67% relative humidity to evaluate their tolerance to adverse conditions of temperature and relative humidity ("RH"). Cultures are prepared from different fermentation batches and are of different age, each having a different long-term stability.

Stressed samples are compared to identical cultures maintained in moisture vapor barrier packaging at 10% relative humidity and 4° C. All samples, stressed and non-stressed, are serially diluted in sterile saline to a concentration of one million cells/ml. A sample of the diluted cells is stained with a commercially available bacteria viability nucleic acid kit (LIVE/DEAD Baclight Viability Kit, Molecular Probes®, Eugene, Oreg.) according to the manufacturer's protocol. The stained sample is analyzed by flow cytometry to measure the cells fluorescing red, green and various hues of yellow and orange.

TABLE 1

Percent Population Live and Intermediate with Increasing Stress (Culture 1)

| Population | Stress Levels (° C./RH) | |
| --- | --- | --- |
| | 4/10 | 37/67 |
| Live | 77.3 | 58.2 |
| Stressed | 3.4 | 17.5 |

TABLE 2

Percent Population Live and Intermediate with Increasing Stress (Culture 2)

| Population | Stress Levels (° C./RH) | |
| --- | --- | --- |
| | 4/10 | 37/67 |
| Live | 53.0 | 40.8 |
| Intermediate | 35.1 | 37.5 |

It can be seen from this example that increasing stress is detected in bacterial cultures by measuring the shift from live to injured cells by fluorescent staining and flow cytometry.

EXAMPLE 3

An overnight grown culture of *Enterococcus faecium* is harvested, washed and resuspended in sterile saline. The washed overnight grown cells are subjected to a high temperature for various times. A suspension of washed overnight grown cells in saline is incubated at 75° C. on a heat block for 3,5,7,10,15, and 30 minutes and then placed on ice. Stressed and non-stressed samples are serially diluted in sterile saline to a concentration of one million cells/ml. A sample of the diluted cells is stained with a commercially available bacteria viability nucleic acid kit (LIVE/DEAD Baclight Viability Kit, Molecular Probes®, Eugene, Oreg.) according to the manufacturer's protocol. The stained sample is analyzed by flow cytometry to measure the fluorescence of red, green and hues of yellow and orange cells.

The shift of live cells to intermediate stressed cells is noted versus the time of incubation. The distribution of the different populations of bacteria is based on their intensity and color fluorescence. In all samples a total of 50,000 particles are analyzed by forward angle light scatter.

An analysis is established to show the different populations. The live population shows intense green fluorescence. The stressed population shows a combination of both red and green stains. Areas described in this protocol are determined by staining separately cell cultures with green (live) and the red (dead) stain.

This stress model shows shifts in populations from live cells to intermediate cells similar to the model described in Example 2, with the exception that this model uses less time and higher temperatures to achieve the same end results. With this stress model quicker evaluations can be made on the culture's survivability after fermentation and prior to lyophilization. Typically, an increase in the intermediate population from less than 10% to no more than 30% and a decline in the live population from greater than 70% to no less than 50% indicates high survivability in commerical products.

EXAMPLE 4

Two lyophilized cultures of *Enterococcus faecium* (cultures 1 and 2) are stored for 10 days in an environment of 67% relative humidity at 37° C., and at 96% relative humidity and 45° C., respectively, to evaluate their tolerance to adverse conditions of temperature and relative humidity. Cultures are prepared from different fermentation batches and are of different age, each having a different long-term stability.

Stressed samples are compared to identical cultures maintained in moisture vapor barrier packaging at 10% relative humidity and 4° C. All samples, stressed and nonstressed, are serially diluted in sterile saline to a concentration of one million cells/ml. A sample of the diluted cells is stained with a commercially available bacteria viability nucleic acid kit (LIVE/DEAD Baclight Viability Kit, Molecular Probes®, Eugene, Oreg.) according to the manufacturer's protocol. The stained sample is analyzed by flow cytometry to measure the cells fluorescing red, green and various hues of yellow and orange.

TABLE 1

Percent Population Live and Intermediate with Increasing Stress (Culture 1)

| Population | Stress Levels (° C./RH) | | |
|---|---|---|---|
| | 4/10 | 37/67 | 45/96 |
| Live | 72.6 | 52.3 | 13.3 |
| Stressed | 8.8 | 20.9 | 67.6 |

TABLE 2

Percent Population Live and Intermediate with Increasing Stress (Culture 2)

| Population | Stress Levels (° C./RH) | | |
|---|---|---|---|
| | 4/10 | 37/67 | 45/96 |
| Live | 77.3 | 35.5 | 63.2 |
| Stressed | 3.3 | 17.6 | 15.2 |

Upon analysis of the initial culture samples, both samples appear suitable for commercial product inclusion. Upon subjecting the culture samples to stress, however, culture 1 is rejected for use because less than 50% of the live cells remain and the percentage of stressed cells are more than 30%. In contrast, culture 2 meets the criteria set forth above in the previous example.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A method of predicting the survivability of a microbial culture comprising measuring the population of stressed cells in the culture and using the measurement as an indicator of survivability, wherein the population of stressed cells is measured by the method comprising the steps of:

(i) staining the culture with a combination of membrane-permeable and membrane-impermeable fluorescent stains;

(ii) quantifying the population of stressed cells by fluorescence measurement.

2. The method of claim 1 wherein the culture is additionally subject to a stress of choice prior to staining.

3. The method of claim 1 wherein the stains are selected from the group consisting of fluorescein diacetate, fluorescein isothiocyanate, chemchrome Y, chemchrome B, rose bengal, calcein acetoxy methyl ester, Hoechst 33342, rhodamine 123, 3,3'-dihexyloxacarbocyanine iodide, Calcofluor white, propidium iodide, 4',6-diamidino-2-phenylindole, ethidium bromide, 3,6-bis(dimethylamino) acridinium chloride, carboxy fluorescein diacetate, and LIVE/DEAD Baclight™ Viability Kit.

4. The method of claim 1 wherein the fluorescence measurement is done by flow cytometry.

5. The method of claim 1 wherein the stress is selected from the group consisting of freeze-drying, nutrient deprivation, chemical injury, pH fluctuations, mechanical injury, long-term storage and changes in temperature and relative humidity.

6. A method of ensuring that a given microbial culture will withstand stress, to meet long term stability and efficacy requirements, comprising measuring the population of stressed cells in the culture and using the measurement as an indicator of survivability of the population, wherein the method of measuring the population of stressed cells comprises the steps of:

(i) staining the culture with a combination of membrane-permeable and membrane-impermeable fluorescent stains;

(ii) quantifying the population of stressed cells by fluorescence measurement.

7. The method of claim 6 wherein the culture is additionally subjected to a stress of choice prior to staining.

8. The method of claim 6 wherein all cultures having a population of stressed cells above 30% are discarded.

* * * * *